United States Patent [19]

Miyatake et al.

[11] Patent Number: 4,499,379
[45] Date of Patent: Feb. 12, 1985

[54] INFRARED RADIATION GAS ANALYZER

[75] Inventors: Kimio Miyatake; Katsuhiko Tomita, both of Kyoto, Japan

[73] Assignee: Horiba, Ltd., Kyoto, Japan

[21] Appl. No.: 473,345

[22] Filed: Mar. 8, 1983

[30] Foreign Application Priority Data

Mar. 9, 1982 [JP] Japan .............................. 57-33702[U]

[51] Int. Cl.³ ................................................ G01J 1/00
[52] U.S. Cl. ...................................... 250/343; 250/352
[58] Field of Search ................... 250/338 R, 343, 344, 250/345, 349, 352; 356/437

[56] References Cited

U.S. PATENT DOCUMENTS

| 3,794,838 | 2/1974 | Weiss et al. | 250/352 |
| 3,968,370 | 7/1976 | Luft | 250/343 |
| 4,233,513 | 11/1980 | Elder et al. | 250/352 |
| 4,320,297 | 3/1982 | Cederstrand et al. | 250/343 |
| 4,373,137 | 2/1983 | Fabinski et al. | 250/343 |

FOREIGN PATENT DOCUMENTS 58-17343  2/1983  Japan ................... 356/437

Primary Examiner—Janice A. Howell
Attorney, Agent, or Firm—Wenderoth, Lind & Ponack

[57] ABSTRACT

An infrared radiation gas analyzer for determining the concentration of an ingredient in a sample gas has a sample gas container for containing a sample gas at a temperature at which the ingredient the concentration of which is to be determined will emit infrared radiation in the range characteristic of the ingredient and a window for allowing the infrared radiation to escape from the container. An optical chopper outside said container interrupts the radiation escaping from the container. A pair of filters is positioned in the path of the radiation escaping from the container and spaced transversely of the path, one of the filters transmitting only radiation in the range and the other of the filters transmitting only radiation in a range near to the first mentioned range. Infrared radiation detectors are positioned for receiving the radiation passed by the respective filters and they emit a signal representative of the difference between the radiation received by the respective detectors and which is representative of the concentration of the ingredient the concentration of which is to be determined in the sample gas.

3 Claims, 4 Drawing Figures

INFRARED RADIATION GAS ANALYZER

BACKGROUND OF THE INVENTION

1. Field of the Invention

The present invention relates to a gas analyzer for determining the concentration of specific ingredients in a sample gas.

2. Description of the Prior Art

The conventional method of determining concentration of ingredients in gas has been by a nondispersive infrared absorption analyzer using Lambert-Beer's law. However, such an analyzer requires an infrared light source and a power source for stabilizing said light source. In addition, it is expensive due to the complicated circuitry. Furthermore, the optical adjustment is required for adjusting the quantity of light incident upon a reference cell and the quantity of light incident upon a sample cell. The reference cell must be provided in order to prevent drift in the light source directing light on said sample cell from occurring.

OBJECTS AND BRIEF DESCRIPTION OF THE INVENTION

It is an object of the present invention to provide an operationally useful infrared radiation gas analyzer which can measure the concentration of ingredients in a gas with high accuracy, and which eliminates the main cause of errors in such measurement.

It is a further object to provide an infrared radiation gas analyzer for determining the concentration of specific ingredients in a sample gas which has simple construction and which is inexpensive.

To this end the present invention provides an infrared light source comprising means to measure an infrared radiation dose of a specified wave length constituted by radiation from gas molecules other than monoatomic molecules and produced by the gas when the gas molecules are heated to high temperatures, whereby an infrared light source and a power source for stabilizing said light source, which have heretofore been required in a conventional infrared gas analyzer, can be dispensed with.

BRIEF DESCRIPTION OF THE DRAWINGS

The invention will now be described in connection with the accompanying drawings, in which.

DESCRIPTION OF THE PREFERRED EMBODIMENT

Figure 1:
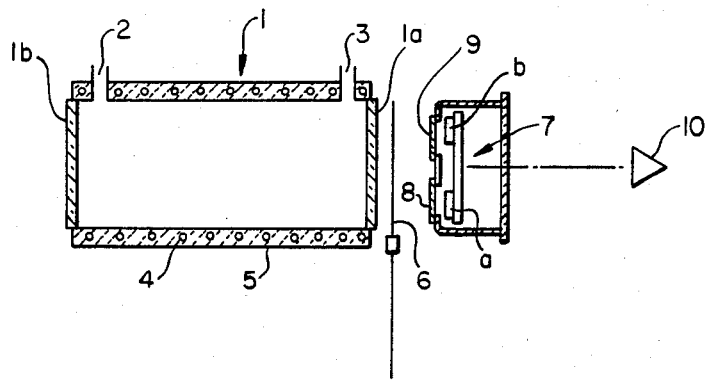
FIG. 1 is a schematic diagram of an infrared radiation gas analyzer according to the invention.

Referring now to FIG. 1, a sample cell 1 has an inlet 2 for a sample gas under a particular pressure and an outlet 3 for the sample gas, the internal surface of said sample cell 1 being a mirror surface, and said sample cell 1 having cell windows 1a and 1b made of infrared ray-transmitting materials at the opposite ends thereof to transmit infrared radiation from within the sample cell. A heater 4 is provided in the wall of cell 1 for heating the sample gas in said sample cell 1, the heater having a capacity to heat the sample gas to temperatures of at least 100° C. to cause it to radiate infrared rays, in order to increase the radiation from a sample gas and decrease the background radiation relative to the radiation from the gas. Insulating material 5 surrounds the elements of heater 4.

A chopper 6 is provided in front of the window 1a, and a dual type infrared detector 7 is provided on the opposite side of the chopper from the window. The detector 7 has two detecting elements a and b which subtracts the two signals from said elements a and b and puts out a differential signal.

A first filter 8 is mounted in front of detecting element a and is for transmitting infrared rays which will be radiated from the ingredient contained in the sample and the concentration of which is to be determined, at the temperature and pressure to which the sample gas is raised, the filter 8 transmitting wave lengths in a specified range W characteristic of the ingredient (for example a 4.3 $\mu$m band of high radiation coefficient when determining the concentration of $CO_2$). The radiation intensity will be in proportion to the concentration of the ingredient.

A second filter 9 is mounted in front of detecting element b and is for transmitting infrared rays having wave lengths in the range W' which is different from the above described specified range W but near the said specified range W.

Said filters 8 and 9 have almost the same transmission factor and half value width.

Accordingly, background infrared rays which are radiated from said cell 1 itself and incident upon said elements a and b are cancelled. Infrared detector 7 detects only a radiation dose of infrared rays radiated from the ingredient the concentration of which is to be determined and which are transmitted only through said first filter 8. Said infrared detector 7 puts out a pulsed electric signal equivalent to the concentration of the ingredient the concentration of which is to be determined due to the operation of chopper 6.

The electric signals from said infrared detector 7 are amplified in amplifier 10. In addition, although not shown in the drawing, the signals, amplified by said amplifier 10, can be outputted in the form of signals equivalent to the concentration of the ingredient the concentration of which is to be determined.

In the above described construction, infrared rays are radiated from a sample gas introduced into said sample cell 1 at a particular pressure and heated to the desired temperature, and simultaneously background infrared rays are radiated from said cell 1 itself when said sample gas is heated to the appointed temperatures by means of said heater 4. The detector 7 with the filters 8 and 9 functions to remove the background radiation so as to leave only the radiation emitted by the ingredient the concentration of which is to be determined.

Figure 2A:
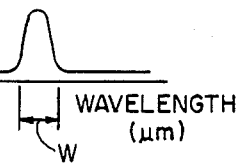
FIGS. 2(a) and 2(b) are graphs showing relative radiation intensity.
Figure 2B:
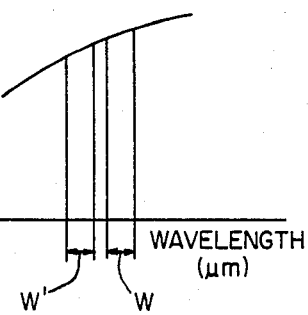

For example, when determining $CO_2$ concentration, said first filter 8 transmits infrared rays A+B, which is the total of infrared rays A radiated from only $CO_2$ and having wave lengths in the specified range W as shown in FIG. 2(a) and infrared rays B having wave lengths in said specified range W forming part of the background infrared rays as shown in FIG. 2(b), while said second filter 9 transmits the background infrared rays B' having wave lengths in the range W' near said specified range W. These background infrared rays are almost equal in intensity as shown in FIG. 2(b), so that B is nearly equal to B'.

When infrared rays A+B and infrared rays B' are radiated onto said detecting elements a and b, respectively, the background infrared rays cancel each other leaving only the dose of radiation from the ingredient, i.e. $A+B-B'\div A$. Thus a radiation dose A of infrared rays radiated from the ingredient the concentration of which is to be determined can be detected by means of said infrared detector 7, and thus the concentration of the ingredient can be accurately determined on the basis of the radiation dose A of infrared rays.

The concentration can also be accurately determined in the same manner as described above even though the amount of background infrared rays is changed because of contamination of said cell 1 and the cell-window 1a and the like, since said infrared detector 7 detects only the concentration of the ingredient to be determined on the basis of absolute values.

Figure 3:
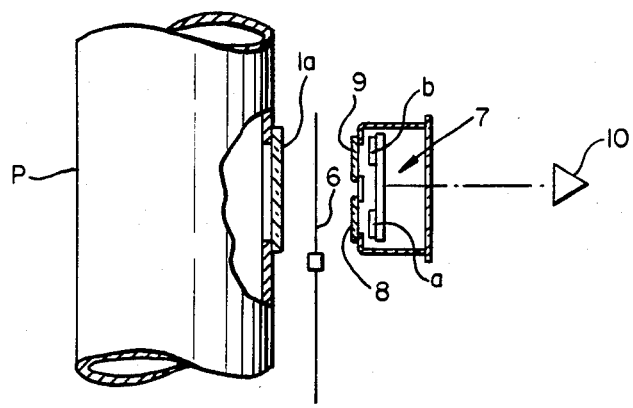
FIG. 3 is a schematic diagram of another embodiment of the present invention.

In addition, although in the above described embodiment the sample gas is heated to the appointed temperatures by means of said heater 4, the sample gas may be heated to a suitable temperature range and temperature compensation may be carried out by using a thermometer for measuring temperatures of gas. Alternatively, gas which has been preliminarily heated to high temperatures can be introduced into said cell 1. Furthermore, exhaust gas pipes P for exhausting exhaust from internal combustion engines and for exhausting gas from factories can constitute said cell, as shown in FIG. 3, and the window 1a can be placed over an aperture in the pipe. The detector 7 and amplifier 10 are the same as in the embodiment shown in FIG. 1.

Furthermore, the concentration of various kinds of ingredients can be detected by using as said first filter 8 and said second filter 9 filters which transmit infrared rays corresponding to those emitted by the ingredients heated to the desired temperatures, and wavelengths near thereto.

In the analyzer according to the present invention, neither an infrared light source nor a power source for stabilizing the light source, which are necessary in the conventional nondispersive infrared absorption analyzer, are required. Furthermore, neither a reference cell nor an optical adjusting mechanism for preventing drift of the light source are required. Thus the concentration of the specified ingredient contained in a sample gas can be determined by an analyzer having a simple and inexpensive construction.

The analyzer of the present invention takes into account that the background infrared rays radiated from said cell and cellwindow is several times or several tens of times as great as the infrared rays radiated from the ingredient of the sample gas. A slight change in temperature can influence the zero point, or the level of infrared rays incident upon the infrared detector may be changed due to a change in the radiation coefficient of the cell, cell-window and the like, and as a result the zero point is changed, which is an important factor causing errors of measurement in the detection of concentration. As a result, the concentration of the specified gaseous ingredient can only be accurately determined by removing the influence of background infrared rays. In the analyzer of the present invention, only the infrared rays radiated from the ingredient to be determined are detected, and this is done by means of the dual type infrared detector which cancels from the total radiation A of infrared rays radiated from the ingredient and having wave lengths in a specified range W and radiation B of background infrared rays having the same wave lengths as the infrared rays radiated from the ingredient, the radiation B by means of the radiation B' of background infrared rays nearly equal to the above described radiation B of background infrared rays.

What is claimed is:

1. An infrared radiation gas analyzer for determining the concentration of an ingredient in a sample gas, comprising:
    a sample gas containing means for containing a sample gas at a temperature at which the ingredient the concentration of which is to be determined will emit infrared radiaton in a range characteristic of the ingredient and means for allowing said infrared radiation to escape from said containing means;
    an optical chopper outside said containing means for interrupting the radiation escaping from said containing means;
    a pair of filters in the path of the radiation escaping from said containing means and spaced transversely of said path, one of said filters transmitting only radiation in said range and the other of said filters transmitting only radiation in a range near to said firstmentioned range;
    infrared radiation detectors positioned for receiving the radiation passed by said respective filters and connected to each other for emitting a signal representative of the difference between the radiation received by the respective detectors and which is representative of the concentration of the ingredient the concentration of which is to be determined in the sample gas.

2. An infrared radiation gas analyzer as claimed in claim 1 in which said sample gas containing means is a sample gas container having heating means for heating a sample gas in said container.

3. An infrared radiation gas analyzer as claimed in claim 1 in which said sample gas containing means is a pipe for carrying a heated gas from a source of heated gas.

* * * * *